(12) United States Patent
Decoster et al.

(10) Patent No.: US 8,246,941 B2
(45) Date of Patent: Aug. 21, 2012

(54) DETERGENT COSMETIC COMPOSITIONS COMPRISING AT LEAST ONE AMINO SILICONE, AND USE THEREOF

(75) Inventors: Sandrine Decoster, Saint Gratien (FR); Sabina Meralli, Vanves (FR)

(73) Assignee: L'Oreal S.A., Paris (FR)

( * ) Notice: Subject to any disclaimer, the term of this patent is extended or adjusted under 35 U.S.C. 154(b) by 686 days.

(21) Appl. No.: 11/439,365

(22) Filed: May 24, 2006

(65) Prior Publication Data

US 2006/0275245 A1    Dec. 7, 2006

Related U.S. Application Data

(60) Provisional application No. 60/688,705, filed on Jun. 9, 2005.

(30) Foreign Application Priority Data

May 24, 2005    (FR) ...................... 05 51349

(51) Int. Cl.
A61K 8/30    (2006.01)
A61Q 5/12    (2006.01)
(52) U.S. Cl. ................. 424/70.24; 424/70.122
(58) Field of Classification Search ................ None
See application file for complete search history.

(56) References Cited

U.S. PATENT DOCUMENTS

| | | |
|---|---|---|
| 2,528,378 A | 10/1950 | Mannheimer |
| 2,781,354 A | 2/1957 | Mannheimer |
| 4,185,087 A | 1/1980 | Morlino |
| 4,217,914 A | 8/1980 | Jacquet et al. |
| 4,240,450 A | 12/1980 | Grollier et al. |
| 4,348,202 A | 9/1982 | Grollier et al. |
| 4,422,853 A | 12/1983 | Jacquet et al. |
| 4,445,521 A | 5/1984 | Grollier et al. |
| 4,579,732 A | 4/1986 | Grollier et al. |
| 4,719,099 A | 1/1988 | Grollier et al. |
| 4,777,040 A | 10/1988 | Grollier et al. |
| 4,803,221 A | 2/1989 | Bair |
| 4,839,166 A | 6/1989 | Grollier et al. |
| 4,948,579 A | 8/1990 | Jacquet et al. |
| 4,970,066 A | 11/1990 | Grollier et al. |
| 4,996,059 A | 2/1991 | Grollier et al. |
| 5,009,880 A | 4/1991 | Grollier et al. |
| 5,089,252 A | 2/1992 | Grollier et al. |
| 5,139,037 A | 8/1992 | Grollier et al. |
| 5,196,189 A | 3/1993 | Jacquet et al. |
| 5,661,118 A | 8/1997 | Cauwet et al. |
| 5,958,392 A | 9/1999 | Grollier et al. |
| 6,153,569 A | 11/2000 | Halloran |
| 6,153,570 A | 11/2000 | Decoster |
| 2002/0006389 A1 | 1/2002 | Restle et al. |
| 2003/0134760 A1* | 7/2003 | Harrison et al. ............. 510/122 |
| 2003/0147842 A1 | 8/2003 | Restle et al. |
| 2003/0157049 A1* | 8/2003 | Gawtrey et al. .......... 424/70.122 |
| 2003/0229948 A1* | 12/2003 | Desenne et al. ................ 8/405 |

FOREIGN PATENT DOCUMENTS

| | | |
|---|---|---|
| EP | 0 095 238 | 11/1983 |
| EP | 0 337 354 | 10/1989 |
| EP | 0 530 974 | 3/1993 |
| EP | 0 739 625 | 10/1996 |
| EP | 0 974 335 | 1/2000 |
| FR | 2 270 846 | 12/1975 |
| FR | 2 383 660 | 10/1978 |
| FR | 2 470 596 | 6/1981 |
| FR | 2 519 863 | 7/1983 |
| FR | 2 598 611 | 11/1987 |
| JP | 8-245984 | 9/1996 |
| JP | 2000-327542 | 11/2000 |
| JP | 2001-311099 | 11/2001 |
| WO | WO 97/46211 | 12/1997 |

OTHER PUBLICATIONS

French Search Report for FR 05/51349, mailed Jan. 13, 2006 (corresponding to the present application).
Japanese Office Action for Japanese Application No. 2006-143298, mailed Aug. 30, 2011.
English language abstract of JP 8-245984, Sep. 24, 1996.
English language abstract of JP 2000-327542, Nov. 28, 2000.
English language abstract of JP 2001-311099, Nov. 9, 2001.

* cited by examiner

*Primary Examiner* — Brian Gulledge
(74) *Attorney, Agent, or Firm* — O'Brien Jones PLLC

(57) ABSTRACT

Disclosed herein is novel detergent and conditioning composition comprising, in a cosmetically acceptable medium, at least one sulfate or sulfonate anionic surfactant, at least one carboxylic anionic surfactant other than the preceding surfactant, at least one amphoteric surfactant and at least one amino silicone, wherein the sulfate or sulfonate anionic surfactant/carboxylic anionic surfactant weight ratio ranges from 2 to 12, and the surfactants are present in the composition in a total amount ranging from 4% to 35% by weight relative to the total weight of the composition. Also disclosed herein is a method for cleansing and/or caring for keratin materials such as the hair or the skin comprising applying this composition to the keratin materials.

23 Claims, No Drawings

DETERGENT COSMETIC COMPOSITIONS COMPRISING AT LEAST ONE AMINO SILICONE, AND USE THEREOF

This application claims benefit of U.S. Provisional Application No. 60/688,705, filed Jun. 9, 2005, the contents of which are incorporated herein by reference. This application also claims benefit of priority under 35 U.S.C. §119 to French Patent Application No. FR 05 51349, filed Apr. 24, 2005, the contents of which are also incorporated herein by reference.

Disclosed herein are cosmetic compositions with improved properties, intended for cleaning and/or conditioning keratin materials such as the hair, and comprising, in a cosmetically acceptable support, at least one sulfate or sulfonate anionic surfactant, at least one carboxylic anionic surfactant different from the preceding surfactant, at least one amphoteric surfactant, and at least one amino silicone. Also disclosed herein is a method for cleansing and/or removing makeup from and/or conditioning keratin materials such as the hair and the skin by applying said compositions to the keratin materials.

It is common practice to use detergent compositions (such as shampoos) based essentially on standard anionic, nonionic, and/or amphoteric surfactants, for example, anionic surfactants, to clean and/or wash keratin materials such as the hair. These compositions may be applied to wet hair and the lather generated by massaging or rubbing with the hands may remove, after rinsing with water, the various types of soiling initially present on the hair and/or the skin.

These base compositions may have good washing power, but the intrinsic cosmetic properties associated therewith nevertheless may be fairly poor, owing, for instance, to the fact that the relatively aggressive nature of such a cleaning treatment can, in the long run, lead to more or less pronounced damage to the hair fiber, this damage being associated, for example, with the gradual removal of the lipids or proteins contained in or on the surface of this fiber.

Thus, in order to improve the cosmetic properties of the above detergent compositions, for example, those that are intended to be applied to sensitized hair (i.e., hair that has been damaged or made brittle, for instance, due to the chemical action of atmospheric agents and/or hair treatments such as permanent-waving, dyeing, and/or bleaching), it is now common practice to introduce additional cosmetic agents known as conditioners into these compositions, these conditioners being intended mainly to repair or limit the harmful or undesirable effects induced by the various treatments or aggressions to which the hair fibers are subjected more or less repeatedly. These conditioners may, of course, also improve the cosmetic behavior of natural hair.

In an attempt to solve this problem, those skilled in the art may use insoluble conditioning agents such as silicones in compositions for caring for keratin materials such as the hair.

However, while these compositions may allow a certain level of improvement in the disentangling and softness of the hair, they unfortunately may also be accompanied by certain cosmetic effects on the hair which are considered undesirable, i.e., lankness of the hairstyle (lack of lightness of the hair), lack of smoothness (hair not uniform from the root to the end), and insufficient sheen.

Furthermore, these insoluble conditioning agents may often not allow transparent or clear compositions to be obtained.

Thus, disclosed herein are compositions that do not have one or more of the drawbacks of the compositions mentioned above.

Conditioning agents may also be conveyed onto the treated keratin materials in order to give them, following application, one or more good cosmetic properties, such as softness, smoothness, sheen, and disentangling properties.

The present inventors have now found that by using a combination of three types of surfactant and at least one amino silicone, it is possible to obtain stable detergent compositions with excellent cosmetic properties, for example, in terms of disentangling, lightness, smoothing out treated hair, and/or having good working properties, such as good intrinsic washing power and good latherability.

In at least one embodiment, the industrial implementation of the presently disclosed compositions is easy and the cosmetic properties of the shampoos are excellent.

The compositions obtained may be stable on storage, without requiring the addition of dispersant and/or of suspension agent for the silicone according to the present disclosure.

In the absence of additional insoluble compounds, the compositions obtained may also be transparent. They may contain large amounts of amino silicone while at the same time maintaining good transparency and having good cosmetic properties.

The compositions in accordance with the present disclosure may have good working properties (for example, an abundant, airy lather that develops quickly) and may also have very good rinsability.

The compositions in accordance with the present disclosure may give keratin materials, such as the hair, a noteworthy treating effect that is manifested, for example, by ease of disentangling, and/or the provision of volume, lightness, smoothness, softness, and/or suppleness without any lankness effect. The hair looks natural, clean, and non-greasy.

Disclosed herein are detergent and conditioning cosmetic compositions, comprising, in a cosmetically acceptable aqueous medium:

(A) at least one sulfate or sulfonate anionic surfactant,
B) at least one carboxylic anionic surfactant other than surfactant (A),
(C) at least one amphoteric surfactant, and
(D) at least one amino silicone, wherein the sulfate or sulfonate anionic surfactant/carboxylic anionic surfactant weight ratio ranges from 2 to 12, and the surfactants are present in the composition in a total amount ranging from 4% to 35% by weight relative to the total weight of the final composition.

Also disclosed herein is a method for cleansing and/or removing makeup from and/or conditioning keratin materials such as the hair and the skin comprising applying said composition to the keratin materials.

Hereinafter, the expression "ranging from x to y" means in the range from x to y, the limits x and y being included.

Surfactants (A) Sulfate or Sulfonate Surfactants

According to the present disclosure, the at least one sulfate or sulfonate anionic surfactant is an anionic surfactant comprising at least one sulfate ($-OSO_3H$ or $-OSO_3^-$) function and/or one sulfonate ($-SO_3H$ or $-SO_3^-$) function.

The sulfate or sulfonate anionic surfactants that may be used, alone or as mixtures, in the context of the present disclosure include, for example, salts (such as alkali metal salts, for instance, sodium, ammonium salts, amine salts, amino alcohol salts, and magnesium salts) of alkyl sulfates, alkylamido sulfates, alkyl ether sulfates, alkylamido ether sulfates, alkylaryl ether sulfates, alkyl ether sulfosuccinates, acyl isethionates, and methyl acyl taurates; the alkyl or acyl radical of these compounds comprising, for example, from 8 to 24 carbon atoms, and the aryl radical being chosen, for example, from phenyl and benzyl groups.

In one embodiment, the average number of ethylene oxide or propylene oxide groups may range from 2 to 50, for example, from 2 to 10.

According to another embodiment, the at least one sulfate or sulfonate anionic surfactant may be chosen from $C_8$-$C_{14}$, for example, $C_{12}$-$C_{14}$, alkyl ether sulfate salts. These salts may comprise from 2 to 5 ethylene oxide groups.

Non-limiting examples of suitable anionic surfactants include sodium, triethanolamine, magnesium, or ammonium ($C_{12}$-$C_{14}$)alkyl sulfates; sodium, ammonium, and magnesium ($C_{12}$-$C_{14}$)alkyl ether sulfates oxyethylenated with 2.2 mol of ethylene oxide; sodium cocoylisethionate; and methyltaurates.

The at least one sulfate or sulfonate anionic surfactant may be present in the composition in an amount ranging from 1.5% to 50% by weight, for example, from 2% to 25% by weight, from 5% to 25% by weight, or from 8% to 20% by weight, relative to the total weight of the composition.

(B) Carboxylic Anionic Surfactants

According to the present disclosure, the at least one carboxylic anionic surfactant is an anionic surfactant comprising at least one carboxylic function (—COOH) optionally in salt form (—COO⁻).

In one embodiment, the at least one carboxylic anionic surfactant other than surfactant (A) may comprise no sulfate or sulfonate functions and may be chosen, for example, from alkyl D-galactoside uronic acids and salts thereof; polyoxyalkylenated ($C_6$-$C_{24}$)alkyl ether carboxylic acids; polyoxyalkylenated ($C_6$-$C_{24}$)alkylaryl ether carboxylic acids and salts thereof; polyoxyalkylenated ($C_6$-$C_{24}$)alkylamido ether carboxylic acids and salts thereof, for example, those comprising from 2 to 50 alkylene oxide groups, for instance, ethylene oxide, such as the compounds sold by Kao under the name AKYPO; ($C_6$-$C_{24}$)acyl sarcosinates and salts thereof; ($C_6$-$C_{24}$)acyl lactylates and salts thereof; and ($C_6$-$C_{24}$)acyl glutamates. ($C_6$-$C_{24}$)Alkylpolyglycoside carboxylic acid esters such as alkylglucoside acetates, alkylglucoside citrates, and alkylpolyglycoside tartrates are also suitable for use herein as carboxylic anionic surfactants. Such products are sold, for example, under the names EUCAROL APG/EC and EUCAROL APG/ET by Lamberti, and PLANTAPON LGC Sorb by Cognis.

Mixtures of these surfactants may also be used.

The salts may be chosen from alkali metal salts such as sodium, ammonium salts, amine salts, salts of amino alcohols such as triethanolamine and monoethanolamine, and magnesium salts.

Anionic surfactants of the polyoxyalkylenated carboxylic ether acid or salt type may include, for example, those of formula (1):

$$R_1—(OC_2H_4)_n—OCH_2COOA \quad (1)$$

wherein:
$R_1$ is chosen from linear or branched $C_8$-$C_{22}$ alkyl radicals, linear or branched $C_8$-$C_{22}$ alkenyl radicals, and mixtures thereof; ($C_8$-$C_9$)alkylphenyl radicals; and $R_2$CONH—CH$_2$—CH$_2$— radicals, wherein $R_2$ is chosen from linear or branched $C_9$-$C_{21}$ alkyl radicals and linear or branched $C_9$-$C_{21}$ alkenyl radicals, n is chosen from integers and decimal numbers (average value) ranging from 2 to 24, for example, from 2 to 10, the alkyl radical comprising from 6 to 20 carbon atoms, for example, from 8 to 18 carbon atoms, and the aryl radical being, in at least one embodiment, a phenyl radical, and A is chosen from hydrogen, ammonium, Na, K, Li, Mg, monoethanolamine residues, and triethanolamine residues.

Mixtures of compounds of formula (1) may also be used, for example, mixtures in which the groups $R_1$ are different.

The oxyalkylenated ether carboxylic acids and salts thereof may be chosen from those of formula (1) in which $R_1$ is chosen from ($C_{12}$-$C_{14}$)alkyl radicals, cocoyl radicals, oleyl radicals, and mixtures thereof; nonylphenyl radicals; and octylphenyl radicals, A is chosen from hydrogen and sodium, and n ranges from 2 to 20, for example, from 2 to 10.

Polyoxyalkylenated ($C_6$-$C_{24}$)alkyl ether carboxylic acids and salts thereof, polyoxyalkylenated ($C_6$-$C_{24}$)alkylamido ether carboxylic acids, for example, those comprising from 2 to 15 alkylene oxide groups, and salts thereof, and mixtures thereof, are also suitable for use herein.

In at least one embodiment, the carboxylic anionic surfactant is chosen from compounds of formula (1) in which $R_1$ is a ($C_{12}$)alkyl radical, A is chosen from hydrogen and sodium, and n ranges from 2 to 10.

Non-limiting examples of suitable commercial products include the products sold by Chem Y under the names:
Akypo® NP 70 (R=nonylphenyl, n=7, p=0, A=H);
Akypo® NP 40 (R=nonylphenyl, n=4, p=0, A=H);
Akypo® OP 40 (R=octylphenyl, n=4, p=0, A=H);
Akypo® OP 80 (R=octylphenyl, n=8, p=0, A=H);
Akypo® OP 190 (R=octylphenyl, n=19, p=0, A=H);
Akypo® RLM 38 (R=($C_{12}$-$C_{14}$)alkyl, n=3.8, p=0, A=H);
Akypo® RLM 38 NV (R=($C_{12}$-$C_{14}$)alkyl, n=4, p=0, A=Na);
Akypo® RLM 45 (R=($C_{12}$-$C_{14}$)alkyl, n=4.5, p=0, A=H);
Akypo® RLM 45 NV (R=($C_{12}$-$C_{14}$)alkyl, n=4.5, p=0, A=Na);
Akypo® RLM 100 (R=($C_{12}$-$C_{14}$)alkyl, n=10, p=0, A=H);
Akypo® RLM 100 NV (R=($C_{12}$-$C_{14}$)alkyl, n=10, p=0, A=Na);
Akypo® RLM 130 (R=($C_{12}$-$C_{14}$)alkyl, n=13, p=0, A=H); and
Akypo® RLM 160 NV (R=($C_{12}$-$C_{14}$)alkyl, n=16, p=0, A=Na);
and the products sold by Sandoz under the names:
SANDOPAN DTC-Acid (R=($C_{13}$)alkyl, n=6, p=0, A=H);
SANDOPAN DTC (R=($C_{13}$)alkyl, n=6, p=0, A=Na);
SANDOPAN LS 24 (R=($C_{12}$-$C_{14}$)alkyl, n=12, p=0, A=Na); and
SANDOPAN JA 36 (R=($C_{13}$)alkyl, n=18, p=0, A=H).

In at least one embodiment, the commercial products may be chosen from
Akypo® RLM 45;
Akypo® RLM 100; and
Akypo® RLM 38.

In another embodiment, the carboxylic anionic surfactant may be chosen from polyoxyalkylenated ($C_6$-$C_{24}$)alkyl ether carboxylic acids and salts thereof; polyoxyalkylenated ($C_6$-$C_{24}$)alkylamido ether carboxylic acids, for example, those comprising from 2 to 15 alkylene oxide groups; and ($C_6$-$C_{24}$) alkylpolyglycoside carboxylic esters and salts thereof, and mixtures thereof.

The at least one carboxylic anionic surfactant other than surfactant (A) may be present in the composition in an amount ranging from 0.5% to 15% by weight, for example, from 1% to 10% by weight, from 1% to 5% by weight, or from 1.5% to 3% by weight relative to the total weight of the composition.

(C) Amphoteric Surfactants:

The amphoteric surfactants, whose nature is not a critical feature in the context of the present disclosure, may be chosen, for example, from aliphatic secondary and tertiary amine derivatives in which the aliphatic radical is a linear or branched chain comprising from 8 to 22 carbon atoms and comprising at least one water-soluble anionic group (for example, carboxylate, sulfonate, sulfate, phosphate, and/or phosphonate); ($C_8$-$C_{20}$)alkylbetaines; sulfobetaines; ($C_8$-$C_{20}$)alkylamido($C_1$-$C_6$)alkylbetaines; and ($C_8$-$C_{20}$)alkylamido($C_1$-$C_6$)alkylsulfobetaines.

Examples of amine derivatives include, but are not limited to, the products described, for example, in U.S. Pat. Nos. 2,528,378 and 2,781,354 and chosen from compounds of formulas (2) and (3):

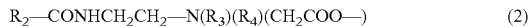

$$R_2\text{—CONHCH}_2\text{CH}_2\text{—N}(R_3)(R_4)(\text{CH}_2\text{COO—}) \quad (2)$$

wherein:
  $R_2$CO is chosen from $C_6$-$C_{24}$ acyl radicals, for example, radicals present in hydrolysed coconut oil, octoyl radicals, decoyl radicals, dodecanoyl radicals, and mixtures thereof,
  $R_3$ is a β-hydroxyethyl group, and
  $R_4$ is a carboxymethyl group;
and

$$R'_2\text{—CONHCH}_2\text{CH}_2\text{—N(B)(C)} \quad (3)$$

wherein:
  B is —CH$_2$CH$_2$OX',
  C is —(CH$_2$)$_n$—Y',
  z is equal to 1 or 2,
  X' is chosen from —CH$_2$CH$_2$—COOH and hydrogen,
  Y' is chosen from —COOH and —CH$_2$—CHOH—SO$_3$H, and
  R'$_2$CO is chosen from $C_6$-$C_{24}$ acyl radicals, for example, radicals present in hydrolysed coconut oil or linseed oil, octoyl radicals, decoyl radicals, dodecanoyl radicals, stearoyl radicals, isostearoyl radicals, oleoyl radicals, and mixtures thereof.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid.

An example of a suitable commercially available amphoteric surfactant is disodium cocoamphodiacetate, sold, for example, under the trade name Miranol® C2M concentrate by Rhodia Chimie.

According to one embodiment of the present disclosure, the at least one amphoteric surfactant may be chosen from those belonging to the betaine group, such as alkylbetaines, for instance, the cocoylbetaine sold under the name DEHYTON AB 30 as an aqueous solution containing 30% AM by Henkel, and alkylamidobetaines, for instance, cocamidopropylbetaine, such as Tegobetaine® F50 sold by Goldschmidt.

The at least one amphoteric surfactant may be present in the composition in an amount ranging from 0.1% to 20% by weight, for example, from 1% to 10% by weight, or from 1.5% to 5% by weight relative to the total weight of the composition.

Thus, according to the present disclosure, the surfactants may be present in the composition in a total amount ranging from 4% to 35% by weight, for example, from 6% to 25% by weight, or from 8% to 20% by weight relative to the total weight of the final composition.

In at least one embodiment, the sulfate or sulfonate anionic surfactant/amphoteric surfactant weight ratio may range from 2 to 12, for example, from 4 to 10, or from 5 to 8.

According to another embodiment, the sulfate or sulfonate anionic surfactant/carboxylic anionic surfactant weight ratio may range from 4 to 10.

In a further embodiment, the carboxylic anionic surfactant/amphoteric surfactant weight ratio may range from 0.3 to 3, for example, from 0.5 to 1.5.

Amino Silicones

The compositions of the present disclosure comprise at least one amino silicone. As used herein, the term "amino silicone" denotes any silicone comprising at least one group chosen from primary amine, secondary amine, tertiary amine, and quaternary ammonium groups. Non-limiting examples of suitable amino silicones include:

a) polysiloxanes of formula (I):

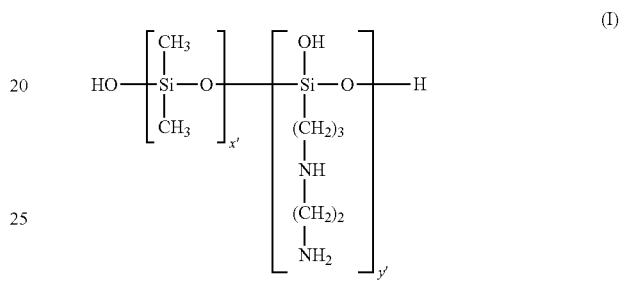

wherein x' and y', which may be identical or different, are integers dependent on the molecular weight, such that the weight-average molecular weight ranges from 5000 to 500 000;

b) amino silicones of formula (II):

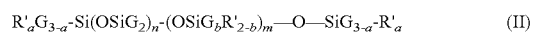

$$R'_aG_{3-a}\text{-Si(OSiG}_2)_n\text{-(OSiG}_bR'_{2-b})_m\text{—O—SiG}_{3-a}\text{-R'}_a \quad (II)$$

wherein:
  G, which may be identical or different, is chosen from hydrogen, phenyl, OH, $C_1$-$C_8$ alkyl groups such as methyl, and $C_1$-$C_8$ alkoxy groups such as methoxy,
  a, which may be identical or different, is an integer ranging from 0 to 3, and in at least one embodiment, 0,
  b is equal to 0 or 1, and in at least one embodiment, 1,
  m and n, which may be identical or different, are numbers such that the sum (n+m) ranges, for example, from 1 to 2000, for instance, from 50 to 150,
  n is a number ranging from 0 to 1999, for example, from 49 to 149,
  m is a number ranging from 1 to 2000, for example, from 1 to 10;
  R', which may be identical or different, is chosen from monovalent radicals of formula —$C_qH_{2q}$L, wherein q is a number ranging from 2 to 8 and L is an optionally quaternized amino group chosen from:
—NR"-Q-N(R")$_2$,
—N(R")$_2$,
—N$^+$(R")$_3$A-,
—N$^+$H(R")$_2$A-,
—N$^+$H$_2$(R")A-,
—N(R")-Q-N$^+$R"H$_2$A-,
—NR"-Q-N$^+$(R")$_2$H A-, and
—NR"-Q-N$^+$(R")$_3$A-,
wherein:
  R" is chosen from hydrogen, phenyl, benzyl, and saturated monovalent hydrocarbon-based radicals, such as $C_1$-$C_{20}$ alkyl radicals;
  Q is a linear or branched group of formula $C_rH_{2r}$, r is an integer ranging from 2 to 6, for example, from 2 to 4; and A- is chosen from halide ions, for instance fluoride, chloride, bromide, and iodide.

Examples of amino silicones corresponding to the above definition include the silicones known as "trimethylsilylamodimethicones", of formula (III):

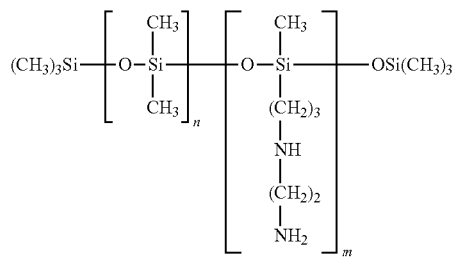

wherein:
- m and n, which may be identical or different, are numbers such that the sum (n+m) ranges, for example, from 1 to 2000, for instance, from 50 to 150,
- n is a number ranging from 0 to 1999, for example, from 49 to 149, and
- m is a number ranging from 1 to 2000, for example, from 1 to 10.

Such polymers are described, for example, in European Patent Application No. 0 095 238.

Another group of amino silicones corresponding to this definition includes silicones of formulas (IV) and (V):

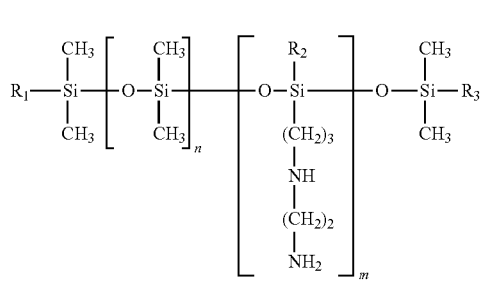

wherein:
- m and n, which may identical or different, are numbers such that the sum (n+m) may range, for example, from 1 to 1000, for instance, from 50 to 250, or from 100 to 200,
- n is a number ranging from 0 to 999, for example, from 49 to 249, or from 125 to 175,
- m is a number ranging from 1 to 1000, for example, from 1 to 10, or from 1 to 5,
- $R_1$, $R_2$, and $R_3$, which may be identical or different, are chosen from hydroxyl and $C_1$-$C_4$ alkoxy radicals, with the proviso that at least one of the radicals $R_1$, $R_2$, and $R_3$ is an alkoxy radical.

In at least one embodiment, the alkoxy radical may be a methoxy radical.

In another embodiment, the hydroxyl/alkoxy molar ratio may range from 0.2:1 to 0.4:1, for example, from 0.25:1 to 0.35:1, or equal to 0.3:1.

The weight-average molecular mass of the silicone may range from 2000 to 1 000 000, for example, from 3500 to 200 000;

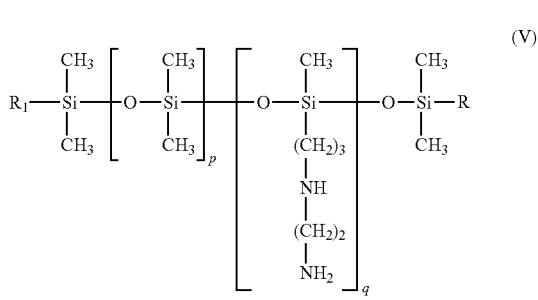

wherein:
- p and q, which may be identical or different, are numbers such that the sum (p+q) may range from 1 to 1000, for example, from 50 to 350, or from 150 to 250,
- p is a number ranging from 0 to 999, for example, from 49 to 349, or from 159 to 239,
- q is a number from 1 to 1000, for example, from 1 to 10, or from 1 to 5;
- $R_1$ and $R_2$, which may be different, are chosen from hydroxyl and $C_1$-$C_4$ alkoxy radicals, with the proviso that at least one of the radicals $R_1$ and $R_2$ is an alkoxy radical.

In at least one embodiment, the alkoxy radical may be a methoxy radical.

The hydroxyl/alkoxy mole ratio may range from 1:0.8 to 1:1.1, for example, from 1:0.9 to 1:1, or may be equal to 1:0.95.

The weight-average molecular mass of the at least one amino silicone of formula (VI) or (V) may range from 2000 to 200 000, for example, from 5000 to 100 000, or from 10 000 to 50 000.

The weight-average molecular mass of the at least one amino silicone of formula (IV) or (V) may be measured by gel permeation chromatography (GPC) at room temperature, as polystyrene equivalents. The columns used are µ styragel columns. The eluent is THF and the flow rate is 1 ml/minute. 200 µl of a solution containing 0.5% by weight of silicone in THF is injected. Detection is performed by refractometry and UV-metry.

Commercial products corresponding to the silicones of structure (IV) and (V) may include at least one other amino silicone whose structure is different from formula (IV) or (V). A commercial product comprising amino silicones of structure (IV) is sold, for example, by Wacker under the name Belsil® ADM 652. A commercial product comprising amino silicones of structure (V) is sold, for example, by Wacker under the name Fluid WR 1300®.

When these amino silicones are used, in at least one embodiment, they may be used in the form of an oil-in-water emulsion. The oil-in-water emulsion may optionally comprise at least one surfactant.

The surfactants may be of any nature, and in at least one embodiment, they may be cationic and/or non-ionic surfactants. The number-average size of the silicone particles in the emulsion may range from 3 nm to 500 nm.

In at least one embodiment, for example, in the case of amino silicones of formula (V), microemulsions with a mean particle size ranging from 5 nm to 60 nm, for example, from 10 nm to 50 nm may be used, for instance, the amino silicone microemulsions of formula (V) sold under the names Finish CT 96 E® or SLM 28020® by Wacker.

In another embodiment, the at least one amino silicone may be chosen such that the contact angle with water of a hair treated with a composition containing 2% (active material) of the silicone according to the present disclosure ranges from 90° to 180°, for example, from 90° to 130°.

To measure the contact angle, the amino silicone may be dissolved or dispersed in a solvent for the amino silicone or for the amino silicone emulsion (for example, hexamethyldisiloxane and water, depending on the hydrophilicity of the silicone).

In at least one embodiment, the composition comprising the at least one amino silicone of formula (IV) or (V) is such that the contact angle with water of hair treated with the composition ranges from 90° to 180°, for example, from 90° to 130°.

The contact angle measurement is based on immersing the hair in distilled water. The measurement comprises evaluating the force exerted by the water on the hair during its immersion in distilled water and during its removal. The forces thus measured are directly related to the contact angle θ between the water and the surface of the hair. The hair is said to be hydrophilic when the angle θ is from 0 to 90°, and hydrophobic when this angle is from 90° to 180°.

The test is performed with locks of natural hair that have been bleached under the same conditions and then washed.

Each 1 g lock is placed in a crystallizing dish 75 mm in diameter and then uniformly covered with 5 mL of the test formulation. The lock is left for 15 minutes at room temperature and then rinsed with distilled water for 30 seconds. The drained lock is left to dry in the open air until it is completely dry.

For each evaluation, 10 hairs that have undergone the same treatment are analyzed. Each sample, attached to a precision microbalance, is immersed via the end in a container filled with distilled water. The DCA ("Dynamic Contact Angle Analyser") balance, from Cahn Instruments, allows measurement of the force (F) exerted by water on the hair.

In parallel, the perimeter of the hair (P) is measured via observation under a microscope.

The mean wettability force on ten hairs and the cross section of the analyzed hairs allows the contact angle of the hair on water to be determined, according to the formula:

$$F = P * \lceil lv * \cos \theta$$

in which

F is the wettability force expressed in Newtons,

P is the perimeter of the hair in meters,

⌈lv is the liquid/vapor interface tension of the water in $J/m^2$, and

θ is the contact angle.

For example, the product SLM 28020 from Wacker at 12% in water (i.e., 2% amino silicone) gives a contact angle of 93° according to the test indicated above. The product Belsil ADM 652 from Wacker at 2% in hexamethyldisiloxane (i.e., 2% amino silicone) gives a contact angle of 111° according to the test indicated above.

Another group of amino silicones corresponding to the definition given above includes compounds of formula (VI):

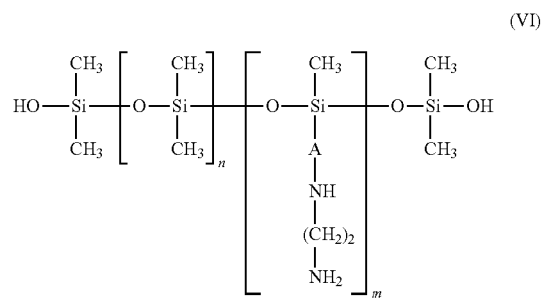

wherein:
m and n, which may be identical or different, are numbers such that the sum (n+m) may range, for example, from 1 to 2000, for instance, from 50 to 150, n is a number ranging from 0 to 1999, for example, from 49 to 149, m is a number ranging from 1 to 2000, for example, from 1 to 10; and A is chosen from linear or branched alkylene radicals comprising from 4 to 8 carbon atoms, for example, 4 carbon atoms. In at least one embodiment, this radical is linear.

The weight-average molecular mass of the at least one amino silicone of formula (VI) may range from 2000 to 1 000 000, for example, from 3500 to 200 000.

The weight-average molecular mass of the at least one amino silicone of formula (VI) may be measured by gel permeation chromatography (GPC) at room temperature, as polystyrene equivalents. The columns used are μ styragel columns. The eluent is THF and the flow rate is 1 ml/minute. 200 μl of a solution containing 0.5% by weight of silicone in THF is injected. Detection is performed by refractometry and UV-metry.

According to at least one embodiment of the present disclosure, the viscosity at 25° C. of the at least one amino silicone of formula (VI) may be greater than 25 000 cSt ($mm^2/s$), for example, ranging from 30 000 to 200 000 cSt ($mm^2/s$), or from 30 000 to 150 000 cSt ($mm^2/s$).

The at least one amino silicone of formula (VI) may have an amine number of less than or equal to 0.4 meq./g, for example, ranging from 0.001 to 0.2 meq./g, or from 0.01 to 0.1 meq./g.

The amine number is the number of amine milliequivalents per gram of compound. This number may be determined in any conventional manner, for example, via titration methods with a colored indicator or via potentiometric titration.

When these amino silicones are used, in at least one embodiment, they may be used in the form of an oil-in-water emulsion. The oil-in-water emulsion may optionally comprise at least one surfactant. The at least one surfactant may be of any nature, but in at least one embodiment, may be chosen from cationic and nonionic surfactants.

The number-average size of the silicone particles in the emulsion may range from 3 nm to 500 nm, for example, from 5 nm to 300 nm, from 10 nm to 275 nm, or from 150 to 275 nm.

A non-limiting example of a corresponding commercial silicone product is, for example, DC2-8299 Cationic Emulsion from Dow Corning.

Another group of amino silicones corresponding to the definition of amino silicones of formula (II) includes compounds of formula (VII):

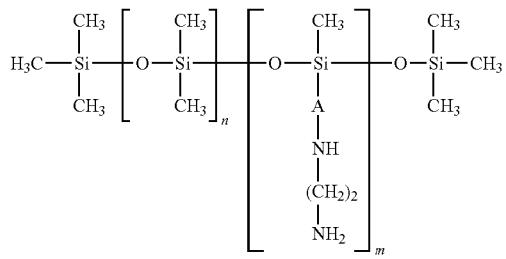

(VII)

wherein:
m and n, which may be identical or different, are numbers such that the sum (n+m) may range, for example, from 1 to 2000, for instance, from 50 to 150;
n is a number ranging from 0 to 1999, for example, from 49 to 149;
m is a number ranging from 1 to 2000, for example, from 1 to 10; and
A is chosen from linear or branched alkylene radicals comprising from 4 to 8 carbon atoms, for example, 4 carbon atoms. In at least one embodiment, this radical may be branched.

The weight-average molecular mass of the at least one amino silicone of formula (VII) may range from 500 to 1 000 000, for example, from 1000 to 200 000.

The weight-average molecular masses of the at least one amino silicone of formula (VII) may be measured by gel permeation chromatography (GPC) at room temperature, as polystyrene equivalents. The columns used are µ styragel columns. The eluent is THF and the flow rate is 1 ml/minute. 200 µl of a solution containing 0.5% by weight of silicone in THF is injected. Detection is performed by refractometry and UV-metry.

According to at least one embodiment of the present disclosure, the viscosity at 25° C. of the amino silicone may be greater than 500 cSt (mm$^2$/s), for example, ranging from 1000 to 200 000 cSt (mm$^2$/s), or from 1500 to 10 000 cSt (mm$^2$/s).

The at least one amino silicone may have an amine number of greater than 0.4 meq./g, for example, ranging from 0.5 to 3 meq./g, or from 0.5 to 1 meq./g.

The amine number is the number of amine milliequivalents per gram of compound. This number may be determined in any conventional manner, for example, via titration methods with a colored indicator or via potentiometric titration.

When these amino silicones are used, in at least one embodiment, they may be used in the form of an oil-in-water emulsion. The oil-in-water emulsion may optionally comprise at least one surfactant. The at least one surfactant may be of any nature, but in at least one embodiment, may be chosen from cationic and nonionic surfactants.

The number-average size of the silicone particles in the emulsion may range from 3 nm to 500 nm, for example, from 5 nm to 300 nm, from 10 nm to 275 nm, or from 150 to 275 nm.

A non-limiting example of a commercial silicone product corresponding to this formula is, for example, DC2-8566 Amino Fluid from Dow Corning.

c) the amino silicones of formula (VIII):

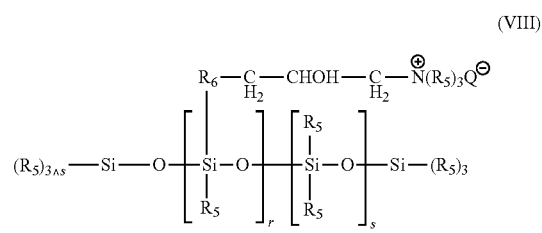

(VIII)

wherein:
$R_5$ is chosen from monovalent hydrocarbon-based radicals comprising from 1 to 18 carbon atoms, for example, $C_1$-$C_{18}$ alkyl radicals, such as methyl, and $C_2$-$C_{18}$ alkenyl radicals;
$R_6$ is chosen from divalent hydrocarbon-based radicals, for example, $C_1$-$C_{18}$ alkylene radicals and divalent $C_1$-$C_{18}$ alkyleneoxy radicals, such as $C_1$-$C_8$, alkyleneoxy radicals, linked to the Si via an Si—C bond;
Q- is an anion chosen, for example, from halide ions, such as chloride, and organic acid salts, such as acetate, etc.;
r is a number representing a mean statistical value ranging from 2 to 20, for example, from 2 to 8;
s is a number representing a mean statistical value ranging from 20 to 200, for example, from 20 to 50.

Such amino silicones are described, for example, in U.S. Pat. No. 4,185,087.

d) the quaternary ammonium silicones of formula (IX):

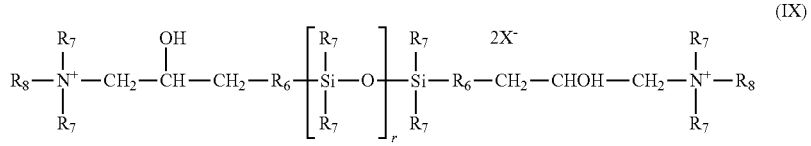

(IX)

wherein:
$R_7$, which may be identical or different, is chosen from monovalent hydrocarbon-based radicals comprising from 1 to 18 carbon atoms, for example, $C_1$-$C_{18}$ alkyl radicals, such as methyl, $C_2$-$C_{18}$ alkenyl radicals, and rings comprising from 5 to 6 carbon atoms;
$R_6$, which may be identical or different, is chosen from divalent hydrocarbon-based radicals, for example, $C_1$-$C_{18}$ divalent alkyleneoxy radicals, such as $C_1$-$C_8$, divalent alkyleneoxy radicals, linked to the Si via an Si—C bond;
$R_8$, which may be identical or different, is chosen from hydrogen and monovalent hydrocarbon-based radicals comprising from 1 to 18 carbon atoms, for example, $C_1$-$C_{18}$ alkyl radicals, $C_2$-$C_{18}$ alkenyl radicals, and —$R_6$—$NHCOR_7$;
X— is an anion chosen, for example, from halide ions, such as chloride, and organic acid salts, such as acetate, etc.;

r is a number representing a mean statistical value ranging from 2 to 200, for example, from 5 to 100.

These silicones are described, for example, in European Patent Application No. 0 530 974.

e) the amino silicones of formula (X):

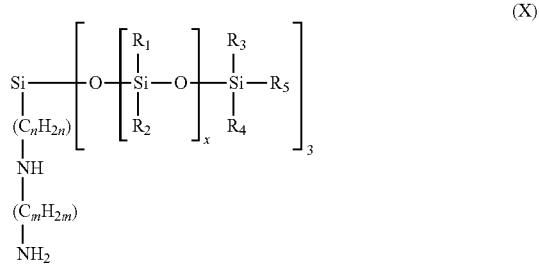

wherein:
R$_1$, R$_2$, R$_3$, and R$_4$, which may be identical or different, are chosen from C$_1$-C$_4$ alkyl radicals and phenyl groups,
R$_5$ is chosen from C$_1$-C$_4$ alkyl radicals and hydroxyl groups,
n is an integer ranging from 1 to 5,
m is an integer ranging from 1 to 5,
x is a number chosen such that the amine number ranges from 0.01 to 1 meq./g.

f) polyoxyalkylenated amino silicones of the type $(XY)_i$, X being a polysiloxane block and Y being a polyoxyalkylene block comprising at least one amine group, which may, for example, comprise repeating units of formula (XI):

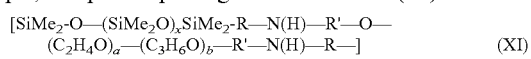

in which:
a is an integer greater than or equal to 1, for example, ranging from 5 to 200, or from 5 to 100;
b is an integer ranging from 0 to 200, for example, from 4 to 200, or from 5 to 100;
x is an integer ranging from 1 to 10 000, for example, from 10 to 5000;
R, which may be identical or different, is chosen from divalent organic groups linked to the adjacent silicon atom via a carbon-silica bond and to a nitrogen atom, and
R', which may be identical or different, is chosen from divalent organic groups linked to the adjacent oxygen atom via a carbon-oxygen bond and to a nitrogen atom.

In at least one embodiment, R may be chose from C$_2$-C$_{12}$ hydrocarbon-based radicals optionally comprising at least one heteroatom, such as oxygen. In another embodiment, R may be chosen from ethylene, linear or branched propylene, linear or branched butylene, and —CH$_2$CH$_2$CH$_2$OCH(OH)CH$_2$— radicals.

In a further embodiment, R' may be chosen from C$_2$-C$_{12}$ hydrocarbon-based radicals optionally comprising at least one heteroatom, such as oxygen. According to one embodiment, R' may be chosen from divalent alkylene radicals, for instance, ethylene, linear or branched propylenes, and linear or branched butylenes.

The siloxane blocks may be present in the silicone in an amount ranging from 50 mol % to 95 mol %, for example, from 70 mol % to 85 mol % relative to the total weight of the silicone.

The amine content may range from 0.02 to 0.5 meq./g, for example, from 0.05 to 0.2 meq./g of copolymer in a 30% solution in dipropylene glycol.

According to at least one embodiment, the weight-average molecular weight of the silicone of formula (XI) may range from 5000 to 1 000 000, for example, from 10 000 to 200 000.

A non-limiting example of a commercial silicone product of formula (XI) is the product sold under the brand name Silsoft A-843 Organosilicone Copolymer by OSI.

In at least one embodiment of the present disclosure, the at least one amino silicone may be chosen from those of formulae (I) and (II), and mixtures thereof. In another embodiment, the at least one amino silicone may be chosen from those of formulae (I) to (VII), for example, those of formulae (I), (IV), (V), (VI), and (VII).

The at least one amino silicone may be present in the composition in an amount ranging from 0.01% to 10% by weight, for example, from 0.1% to 5% by weight, or from 0.5% to 3% by weight, relative to the total weight of the composition.

According to one embodiment of the present disclosure, the compositions may further comprise at least one water-soluble salt and/or a mono- or polyhydroxylated water-soluble alcohol. The water-soluble salts according to the present disclosure may be chosen, for example, from salts of monovalent metals, divalent metals, mineral acids, and organic acids.

Examples of water-soluble salts include, but are not limited to, sodium chloride, potassium chloride, calcium chloride, magnesium sulfate, sodium citrate, and the sodium salts of phosphoric acid. In at least one embodiment, the at least one water-soluble salt may be sodium chloride.

The detergent compositions according to the present disclosure may have a final pH ranging, for example, from 3 to 8, for instance, from 4 to 7.5. The pH may be adjusted to the desired value by adding a base (for example, organic and mineral bases) to the composition, for example, sodium hydroxide, aqueous ammonia, and primary, secondary, and tertiary (poly)amines, for instance, monoethanolamine, diethanolamine, triethanolamine, isopropanolamine, and 1,3-propanediamine, or by adding an acid chosen from mineral and organic acids, such as citric acid and hydrochloric acid.

The cosmetically acceptable aqueous medium may be chosen from water and mixtures of water and of a cosmetically acceptable solvent, such as C$_1$-C$_4$ lower alcohols, for instance, ethanol, isopropanol, tert-butanol, and n-butanol; and alkylene glycols, for instance, propylene glycol, hexylene glycol, and glycerol.

The composition according to the present disclosure may comprise water in an amount of at least 30% by weight, for example, from 50% to 90% by weight, or from 70% to 85% by weight, relative to the total weight of the composition.

In at least one embodiment, the composition may comprise less than 20% by weight of fatty phase relative to the total weight of the composition.

The fatty phase may comprise all the fatty substances of the composition that are insoluble in water at room temperature, such as, fatty esters, plant, mineral and synthetic oils, fatty alcohols, fatty acids, fatty amides, waxes, and silicones. The fatty phase may be present in the composition in an amount ranging from 0.1% to 15% by weight, for example, from 0.5% to 10% by weight, or from 0.5% to 8% by weight, relative to the total weight of the composition.

The compositions in accordance with the present disclosure may comprise, in addition to the components defined above, at least one viscosity regulator, such as at least one thickener. Examples of viscosity regulators include, but are not limited to, scleroglucans, xanthan gums, fatty acid alkanolamides, alkyl ether carboxylic acid alkanolamides optionally oxyethylenated with up to 5 mol of ethylene oxide, such as the product sold under the name AMINOL A15 by Chem Y, crosslinked polyacrylic acids, and crosslinked acrylic acid/$C_{10}$-$C_{30}$ alkyl acrylate copolymers. The at least one viscosity regulator may be present in the compositions according to the present disclosure in an amount less than or equal to 10% by weight relative to the total weight of the composition.

The compositions in accordance with the present disclosure may also comprise at least one nacreous agent or opacifier, which may be present in the composition in an amount of less than equal to 5%. The at least one nacreous agent or opacifier may be chosen from those known in the art, for instance, fatty alcohols, sodium palmitate, magnesium palmitate, sodium stearate, magnesium stearate, hydroxystearate, fatty alcohols, fatty-chain acyl derivatives such as ethylene glycol and polyethylene glycol distearates, and fatty-chain ethers, for instance distearyl ether and 1-(hexadecyloxy)-2-octadecanol.

The compositions in accordance with the present disclosure may also optionally contain other agents which may improve the cosmetic properties of the hair or the skin without, however, impairing the stability of the compositions. Non-limiting examples of optional additives include cationic surfactants; anionic polymers; nonionic polymers; cationic polymers; amphoteric polymers; proteins; protein hydrolysates; ceramides; pseudoceramides; plant oils; fatty acids, for example, those comprising linear or branched $C_{16}$-$C_{40}$ chains such as 18-methyleicosanoic acid; hydroxy acids; vitamins; provitamins such as panthenol; volatile and non-volatile silicones other than the amino silicones, which may be soluble or insoluble in the medium; UV-screening agents; moisturizers; antidandruff agents, anti-seborrhoeic agents; hair-loss counteractants; free-radical scavengers; and mixtures thereof.

According to one embodiment, the compositions according to the present disclosure may also comprise at least one cationic polymer.

The at least one cationic polymer may be chosen from those known in the art for improving the cosmetic properties of hair treated with detergent compositions, for example, those described in European Patent Application No. 0 337 354 and French Patent Application Nos. 2 270 846, 2 383 660, 2 598 611, 2 470 596, and 2 519 863.

As used herein, the expression "cationic polymer" denotes any polymer comprising at least one cationic groups and/or group that can be ionized into a cationic group.

In one embodiment, the at least one cationic polymer may have a cationic charge density of greater than or equal to 0.01 meq./g, for example, ranging from 0.1 to 3.5 meq./g.

Examples of suitable cationic polymers include, but are not limited to, quaternary cellulose ether derivatives, such as the products sold under the name JR 400 by Union Carbide Corporation; cyclopolymers, such as diallyldimethylammonium salt homopolymers and copolymers of a diallyldimethylammonium salt and of acrylamide, for instance, the chlorides, sold, for example, under the names MERQUAT 550 and MERQUAT S by Merck; cationic polysaccharides, such as guar gums modified with 2,3-epoxy-propyltrimethylammonium chloride, sold, for example, under the name JAGUAR C13S by Meyhall; optionally crosslinked homopolymers and copolymers of (meth)acryloyloxyethyl-trimethylammonium salt, sold, for example, by Allied Colloids as a 50% solution in mineral oil under the trade names SALCARE SC92 (crosslinked copolymer of methacryloyloxyethyl-trimethylammonium chloride and of acrylamide) and SALCARE SC95 (crosslinked homopolymer of methacryloyloxyethyltrimethylammonium chloride); and quaternary copolymers of vinylpyrrolidone and of a vinylimidazole salt, such as the products sold by BASF under the names LUVIQUAT FC 370, LUVIQUAT FC 550, LUVIQUAT FC 905, and LUVIQUAT HM-552.

According to one embodiment of the present disclosure, the at least one cationic polymer may be present in the composition in an amount ranging from 0.005% to 10% by weight, for example, from 0.01% to 5% by weight, or from 0.1% to 3% by weight relative to the total weight of the final composition.

The compositions according to the present disclosure may also contain foam synergists such as $C_{10}$-$C_{18}$ 1,2-alkanediols and $C_{10}$-$C_{18}$ fatty alkanolamides derived from monoethanolamine or from diethanolamine.

It is to be understood that a person skilled in the art will take care to select the at least one optional additional compound and/or the amounts thereof such that the solubility of the amino silicones according to the present disclosure, the stability of the composition, and the cosmetic properties intrinsically associated with the composition in accordance with the present disclosure are not, or are not substantially, adversely affected by the envisaged addition. The addition of certain compounds such as nacreous agents may make the composition non-transparent.

The transparency may be determined by measuring the transmittance at 700 nm via a spectrometer (for example a Lambda 14 spectrometer from Perkin-Elmer or a UV2101 PC spectrometer from Shimadzu). In one embodiment, the transparent compositions may have a transmittance of greater than or equal to 94%, for example, ranging from 96% to 100%.

The latherability of the compositions according to the present disclosure, characterized by a foam height, may be greater than 75 mm, for example, greater than 100 mm, measured according to the amended Ross-Miles method (NF T 73-404/ISO696).

The amendments to the method are as follows:

Measurement is performed at a temperature of 22° C. with osmosed water. The concentration of the solution is 2 g/l. The height of the drop is 1 m. The amount of composition that is dropped is 200 ml. These 200 ml of composition fall into a measuring cylinder with a diameter of 50 mm and containing 50 ml of the test composition. The measurement is taken 5 minutes after stopping the flow of the composition.

The compositions in accordance with the present disclosure may be in the form of thickened liquids, creams, and gels, and they may be suitable for washing and caring for keratin materials, such as the hair and the skin, and in at least one embodiment, the hair.

Also disclosed herein is a process for washing and conditioning keratin materials such as the hair, which comprises applying to the keratin materials, which may optionally be wet, an effective amount of a composition as defined above, and then in rinsing with water after an optional leave-in time.

The compositions according to the present disclosure may be used as shampoos for washing and/or conditioning the hair, and they may be applied, in this case, to wet hair in amounts that are suitable to wash the hair, and the lather generated by massaging or rubbing with the hands may be removed after an optional leave-in time, by rinsing with water, the operation possibly being repeated at least one time.

The compositions in accordance with the present disclosure may also be used as shower gels for washing and/or conditioning the hair and/or the skin, in which case they may be applied to the wet skin and/or hair and may be rinsed off after application.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below.

EXAMPLES

The following shampoo compositions in accordance with the present disclosure were prepared:

| | 1 | 2 | 3 |
|---|---|---|---|
| Sodium lauryl ether sulfate (70/30 C12/C14) containing 2.2 mol of ethylene oxide, as an aqueous solution containing 70% AM | 14.2 g AM | 14.2 g AM | 10 g AM |
| Sodium N-methyl-N-cocoyl taurate at 30% AM in water (Hostapon LT-SF from Clariant) | — | — | 3 g AM |
| Cocoylbetaine containing 30% AM (Dehyton AB 30) | 1.9 g AM | 1.9 g AM | — |
| Disodium cocoamphodiacetate at 39% AM in water (Miranol C2M Conc. from Rhodia Chimie) | — | — | 3 g AM |
| Lauryl ether carboxylic acid at 90% AM in water (Akypo RLM 45 CA from Kao) | 1.8 g AM | 1.8 g AM | — |
| Triethanolamine cocoylglutamate as an aqueous solution containing 30% AM (Amisoft CT12 from Ajinomoto) | — | — | 2 g AM |
| Amino silicone (DC2-8566 Amino Fluid from Dow Corning) | 1 g | | 1 g |
| Amino silicone (DC2-8299 Cationic Emulsion from Dow Corning) | | 0.5 g AM | |
| Cationic cellulose (JR400 from Amerchol) | 1 g | 1 g | 1 g |
| Coconut acid monoisopropanolamide | 3.3 g | 3.3 g | 3.3 g |
| Fragrance, preserving agent | qs | qs | qs |
| Hydrochloric acid qs pH | 5-5.6 | 5-5.6 | 5-5.6 |
| Demineralized water qs | 100 g | 100 g | 100 g |
| Transmittance at 700 nm | >94% | >94% | >94% |

The compositions were transparent and stable. When the compositions were applied to wet hair, the lather was abundant and airy, it started easily and rinsed out easily and quickly.

Hair treated with these compositions disentangled easily and was light and smooth from the root to the end.

What is claimed is:

1. A detergent and conditioning cosmetic composition, comprising, in a cosmetically acceptable aqueous medium,
   (A) at least one sulfate or sulfonate anionic surfactant in an amount ranging from 8% to 25% by weight relative to the total weight of the composition,
   (B) at least one carboxylic anionic surfactant other than surfactant (A) in an amount ranging from 0.5% to 15% by weight relative to the total weight of the composition,
   (C) at least one amphoteric surfactant in an amount ranging from 1% to 10% by weight relative to the total weight of the composition, and
   (D) at least one amino silicone,
   wherein the at least one carboxylic anionic surfactant is chosen from those of formula (1):

$$R_1-(OC_2H_4)_n-OCH_2COOA \qquad (1)$$

wherein:
   $R_1$ is chosen from linear or branched $C_8$-$C_{22}$ alkyl radicals, linear or branched $C_8$-$C_{22}$ alkenyl radicals, and mixtures thereof; ($C_8$-$C_9$)alkylphenyl radicals; and $R_2$CONH—$CH_2$—$CH_2$— radicals, wherein $R_2$ is chosen from linear or branched $C_9$-$C_{21}$ alkyl radicals and linear or branched $C_9$-$C_{21}$ alkenyl radicals,
   n is chosen from integers and decimal numbers (average value) ranging from 2 to 24, and
   A is chosen from hydrogen, ammonium, Na, K, Li, Mg, monoethanolamine residues, and triethanolamine residues;
   wherein the at least one sulfate or sulfonate anionic surfactant and the at least one carboxylic anionic surfactant are present in a weight ratio ranging from 2 to 10,
   wherein the weight ratio of the at least one sulfate or sulfonate anionic surfactant to the at least one amphoteric surfactant ranges from 4 to 10,
   and wherein the at least one carboxylic anionic surfactant and the at least one amphoteric surfactant are present in a weight ratio ranging from 0.3 to 1.5, and
   the surfactants are present in the composition in a total amount ranging from 8% to 35% by weight relative to the total weight of the composition.

2. The composition of claim 1, wherein the at least one carboxylic anionic surfactant is present in the composition in an amount ranging from 1% to 10% by weight relative to the total weight of the composition.

3. The composition of claim 1, wherein the weight ratio of the at least one sulfate or sulfonate anionic surfactant to the at least one amphoteric surfactant ranges from 5 to 8.

4. The composition of claim 1, wherein the weight ratio of the at least one sulfate or sulfonate anionic surfactant to the at least one carboxylic anionic surfactant ranges from 4 to 10.

5. The composition of claim 1, wherein the at least one amino silicone is chosen from:
   a) polysiloxanes of formula (I):

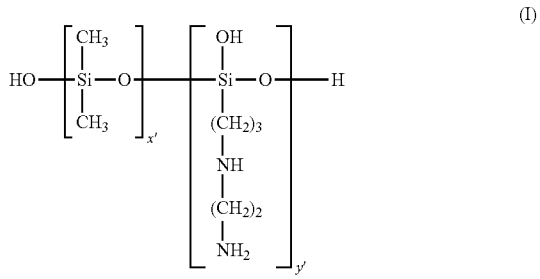

wherein x' and y' are integers such that the weight-average molecular weight ranges of the polysiloxanes of formula (I) ranges from 5000 to 500,000;

b) amino silicones of formula (II):

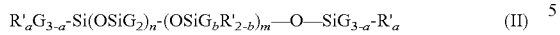

wherein:
G, which may be identical or different, is chosen from hydrogen, phenyl, OH, $C_1$-$C_8$ alkyl, and $C_1$-$C_8$ alkoxy groups,
a, which may be identical or different, is an integer from 0 to 3,
b is equal to 0 or 1,
m and n are numbers such that the sum (n+m) ranges from 1 to 2000,
n is a number ranging from 0 to 1999,
m is a number from 1 to 2000; and
R', which may be identical or different, is chosen from monovalent radicals of formula —CqH2qL in which q is a number ranging from 2 to 8 and L is an optionally quaternized amino group chosen from:
—NR"-Q-N(R")$_2$,
—N(R")$_2$,
—N$^+$(R")$_3$A-,
—N$^+$H(R")$_2$A-,
—N$^+$H$_2$(R")A-,
—N(R")-Q-N$^+$R"H$_2$A-,
—NR"-Q-N$^+$(R")$_2$HA-, and
—NR"-Q-N$^+$(R")$_3$A-,
in which R" is chosen from hydrogen, phenyl, benzyl, and saturated monovalent hydrocarbon-based radicals; Q is chosen from linear or branched groups of formula $C_rH_{2r}$, r is an integer ranging from 2 to 6; and A- is a halide ion;

c) amino silicones of formula (VIII):

$$\begin{array}{c} R_6-\underset{H_2}{C}-CHOH-\underset{H_2}{C}-\overset{\oplus}{N}(R_5)_3Q^{\ominus} \\ | \\ (R_5)_{3\wedge s}-Si-O-\left[\begin{array}{c} | \\ Si-O \\ | \\ R_5 \end{array}\right]_n \left[\begin{array}{c} R_5 \\ | \\ Si-O \\ | \\ R_5 \end{array}\right]_s -Si-(R_5)_3 \end{array} \quad (VIII)$$

wherein:
$R_5$ is chosen from monovalent hydrocarbon-based radicals comprising from 1 to 18 carbon atoms;
$R_6$ is chosen from divalent hydrocarbon-based radicals linked to the Si via an Si—C bond;
Q- is an anion chosen from halides and organic acid salts;
r is a number representing a mean statistical value ranging from 2 to 20; and
s is a number representing a mean statistical value ranging from 20 to 200;

d) quaternary ammonium silicones of formula (IX):

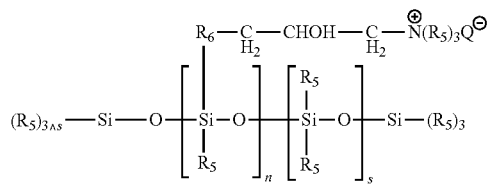

wherein:
$R_7$, which may be identical or different, is chosen from monovalent hydrocarbon-based radicals comprising from 1 to 18 carbon atoms;
$R_6$, which may be identical or different, is chosen from divalent hydrocarbon-based radicals linked to the Si via an Si—C bond;
$R_8$, which may be identical or different, is chosen from hydrogen and monovalent hydrocarbon-based radicals comprising from 1 to 18 carbon atoms;
X— is an anion chosen from halides and organic acid salts; and
r is a number representing a mean statistical value ranging from 2 to 200;

e) amino silicones of formula (X):

$$\begin{array}{c} Si-\left[O-\left[\begin{array}{c} R_1 \\ | \\ Si-O \\ | \\ R_2 \end{array}\right]_x \begin{array}{c} R_3 \\ | \\ Si-R_5 \\ | \\ R_4 \end{array}\right]_3 \\ (C_nH_{2n}) \\ | \\ NH \\ | \\ (C_mH_{2m}) \\ | \\ NH_2 \end{array} \quad (X)$$

wherein:
$R_1$, $R_2$, $R_3$, and $R_4$, which may be identical or different, are chosen from $C_1$-$C_4$ alkyl radicals and phenyl groups,
$R_5$ is chosen from $C_1$-$C_4$ alkyl radicals and hydroxyl groups,
n is an integer ranging from 1 to 5,
m is an integer ranging from 1 to 5,
x is a number chosen such that the amine number ranges from 0.01 to 1 meq./g; and f) polyoxyalkylenated amino silicones of type $(XY)_i$, wherein X is a polysiloxane block and Y is a polyoxyalkylene block comprising at least one amine group.

6. The composition of claim 5, wherein in the polyoxyalkylenated amino silicones of type $(XY)_i$, Y is a polyoxyalkylene block comprising repeating units of formula (XI):

[SiMe$_2$-O—(SiMe$_2$O)$_x$SiMe$_2$-R—N(H)—R'—O—(C$_2$H$_4$O)$_a$—(C$_3$H$_6$O)$_b$—R'—N(H)—R—] (XI)

wherein:
a is an integer greater than or equal to 1;
b is an integer ranging from 0 to 200;
x is an integer ranging from 1 to 10 000;
R, which may be identical or different, is chosen from divalent organic groups linked to the adjacent silicon atom via a carbon-silica bond and to a nitrogen atom, and R', which may be identical or different, is chosen from divalent organic groups linked to the adjacent oxygen atom via a carbon-oxygen bond and to a nitrogen atom.

7. The composition of claim 6, wherein
a is an integer ranging from 5 to 100;
b is an integer ranging from 5 to 100; and
x is an integer ranging from 10 to 5000.

8. The composition of claim 5, wherein the at least one amino silicone is chosen from amino silicones of formulas (I) and (II), and mixtures thereof.

9. The composition of claim 1, wherein the at least one amino silicone is chosen from silicones of formulas (VI) and (VII):

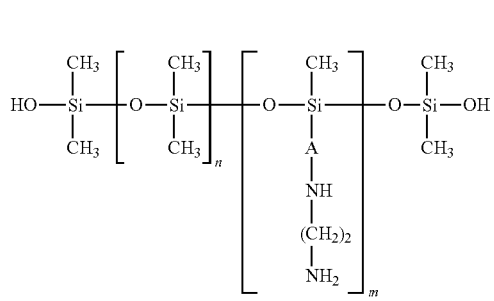
(VI)

wherein:
m and n are numbers such that the sum (n+m) ranges from 1 to 2000;
n is a number ranging from 0 to 1999;
m is a number from 1 to 2000; and
A is chosen from linear or branched alkylene radicals comprising from 4 to 8 carbon atoms;

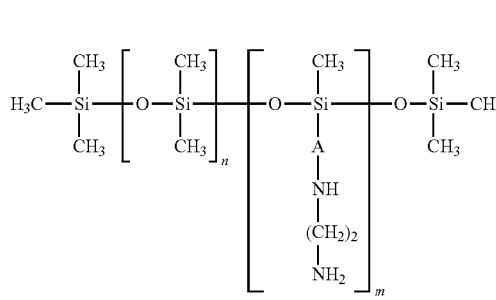
(VII)

wherein:
m and n are numbers such that the sum (n+m) ranges from 1 to 2000;
n is a number ranging from 0 to 1999;
m is a number ranging from 1 to 2000; and
A is chosen from linear or branched alkylene radicals comprising from 4 to 8 carbon atoms.

10. The composition of claim 1, wherein the at least one amino silicone is present in the composition in an amount ranging from 0.01% to 10% relative to the total weight of the composition.

11. The composition of claim 10, wherein the at least one amino silicone is present in the composition in an amount ranging from 0.1% to 5% relative to the total weight of the composition.

12. The composition of claim 11, wherein the at least one amino silicone is present in the composition in an amount ranging from 0.5% to 3% by weight relative to the total weight of the composition.

13. The composition of claim 1, further comprising at least one cationic polymer.

14. The composition of claim 13, wherein the at least one cationic polymer is chosen from quaternary cellulose ethers, copolymers of a diallyldimethylammonium salt and of acrylamide, cationic polysaccharides, and quaternary copolymers of vinylpyrrolidone and of a vinylimidazole salt.

15. The composition of claim 13, wherein the at least one cationic polymer is present in the composition in an amount ranging from 0.005% to 10% by weight relative to the total weight of the composition.

16. The composition of claim 15, wherein the at least one cationic polymer is present in the composition in an amount ranging from 0.01% to 5% by weight relative to the total weight of the composition.

17. The composition of claim 16, wherein the at least one cationic polymer is present in the composition in an amount ranging from 0.1% to 3% by weight relative to the total weight of the composition.

18. The composition of claim 1, wherein the cosmetically acceptable aqueous medium is chosen from water and mixtures of water and at least one cosmetically acceptable solvent.

19. The composition of claim 18, wherein the at least one solvent is chosen from $C_1$-$C_4$ lower alcohols, alkylene glycols, and glycerol.

20. The composition of claim 19, wherein the $C_1$-$C_4$ lower alcohols are chosen from ethanol, isopropanol, tert-butanol, and n-butanol, and wherein the alkylene glycols are chosen from propylene glycol and hexylene glycol.

21. The composition of claim 1, further comprising at least one adjuvant chosen from cationic surfactants; anionic, non-ionic, and amphoteric polymers; proteins; protein hydrolysates; ceramides; pseudoceramides; plant oils; fatty acids; hydroxy acids; vitamins; provitamins; volatile or non-volatile non-amino silicones, which may be soluble or insoluble in the medium; UV-screening agents; moisturizers; antidandruff agents; anti-seborrhoeic agents; hair-loss counteractants; free-radical scavengers; opacifiers; and mixtures thereof.

22. A method for cleansing and/or removing makeup from keratin materials comprising applying a cosmetic composition to the keratin materials, wherein the cosmetic composition comprises, in a cosmetically acceptable aqueous medium,
(A) at least one sulfate or sulfonate anionic surfactant in an amount ranging from 8% to 25% by weight relative to the total weight of the composition,
(B) at least one carboxylic anionic surfactant other than surfactant (A) in an amount ranging from 0.5% to 15% by weight relative to the total weight of the composition,
(C) at least one amphoteric surfactant in an amount ranging from 1% to 10% by weight relative to the total weight of the composition, and
(D) at least one amino silicone,
wherein the at least one carboxylic anionic surfactant is chosen from those of formula (1):

wherein:
$R_1$ is chosen from linear or branched $C_8$-$C_{22}$ alkyl radicals, linear or branched $C_8$-$C_{22}$ alkenyl radicals, and mixtures thereof; $(C_8$-$C_9)$alkylphenyl radicals; and $R_2$CONH—$CH_2$—$CH_2$— radicals, wherein $R_2$ is chosen from linear or branched $C_9$-$C_{21}$ alkyl radicals and linear or branched $C_9$-$C_{21}$ alkenyl radicals,
n is chosen from integers and decimal numbers (average value) ranging from 2 to 24, and A is chosen from hydrogen, ammonium, Na, K, Li, Mg, monoethanolamine residues, and triethanolamine residues;

wherein the at least one sulfate or sulfonate anionic surfactant and the at least one carboxylic anionic surfactant are present in a weight ratio ranging from 2 to 10, wherein the weight ratio of the at least one sulfate or sulfonate anionic surfactant to the at least one amphoteric surfactant ranges from 4 to 10, and wherein the at least one carboxylic anionic surfactant and the at least one amphoteric surfactant are present in a weight ratio ranging from 0.3 to 1.5, and the surfactants are present in the composition in a total amount ranging from 8% to 35% by weight relative to the total weight of the final composition.

23. A process for washing and/or conditioning keratin materials, comprising applying to the keratin materials an effective amount of a cosmetic composition, and then in rinsing with water after an optional leave-in time, wherein the keratin materials may optionally be wet before application of the cosmetic composition;

the cosmetic composition comprises, in a cosmetically acceptable aqueous medium, (A) at least one sulfate or sulfonate anionic surfactant in an amount ranging from 8% to 25% by weight relative to the total weight of the composition, (B) at least one carboxylic anionic surfactant other than surfactant (A) in an amount ranging from 0.5% to 15% by weight relative to the total weight of the composition, (C) at least one amphoteric surfactant in an amount ranging from 1% to 10% by weight relative to the total weight of the composition, and, and (D) at least one amino silicone, wherein the at least one carboxylic anionic surfactant is chosen from those of formula (1):

$$R_1-(OC_2H_4)_n-OCH_2COOA \qquad (1)$$

wherein:

$R_1$ is chosen from linear or branched $C_8$-$C_{22}$ alkyl radicals, linear or branched $C_8$-$C_{22}$ alkenyl radicals, and mixtures thereof; ($C_8$-$C_9$)alkylphenyl radicals; and $R_2CONH-CH_2-CH_2-$ radicals, wherein $R_2$ is chosen from linear or branched $C_9$-$C_{21}$ alkyl radicals and linear or branched $C_9$-$C_{21}$ alkenyl radicals, n is chosen from integers and decimal numbers (average value) ranging from 2 to 24, and A is chosen from hydrogen, ammonium, Na, K, Li, Mg, monoethanolamine residues, and triethanolamine residues;

the at least one sulfate or sulfonate anionic surfactant and the at least one carboxylic anionic surfactant are present in a weight ratio ranging from 2 to 10, wherein the weight ratio of the at least one sulfate or sulfonate anionic surfactant to the at least one amphoteric surfactant ranges from 4 to 10, and wherein the at least one carboxylic anionic surfactant and the at least one amphoteric surfactant are present in a weight ratio ranging from 0.3 to 1.5, and the surfactants are present in the composition in a total amount ranging from 8% to 35% by weight relative to the total weight of the final composition.

* * * * *